US012508378B1

(12) United States Patent
Erickson et al.

(10) Patent No.: US 12,508,378 B1
(45) Date of Patent: Dec. 30, 2025

(54) BREATHE ASSIST SYSTEM AND BREATHE ASSIST CONTROL SYSTEM

(71) Applicant: Triad National Security, LLC, Los Alamos, NM (US)

(72) Inventors: George Andrew Erickson, Los Alamos, NM (US); Kory William Sylvester, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 902 days.

(21) Appl. No.: 17/381,130

(22) Filed: Jul. 20, 2021

Related U.S. Application Data

(60) Provisional application No. 63/054,151, filed on Jul. 20, 2020.

(51) Int. Cl.
*A61M 16/00* (2006.01)
*A61M 16/10* (2006.01)
*A61M 16/20* (2006.01)

(52) U.S. Cl.
CPC .... *A61M 16/0081* (2014.02); *A61M 16/0003* (2014.02); *A61M 16/0051* (2013.01); *A61M 16/026* (2017.08); *A61M 16/105* (2013.01); *A61M 16/208* (2013.01); *A61M 2016/0024* (2013.01); *A61M 2016/0027* (2013.01); *A61M 2016/0036* (2013.01); *A61M 2016/103* (2013.01); *A61M 2205/103* (2013.01); *A61M 2205/3334* (2013.01); *A61M 2230/42* (2013.01); *A61M 2230/432* (2013.01)

(58) Field of Classification Search
CPC ........... A61M 16/0051; A61M 16/0078–0084; A61M 16/105; A61M 2016/0027; A61M 2016/003; A61M 2016/0036; A61M 2205/103; A61M 2205/3334; A61M 2230/42; A61M 2230/432
USPC ....................................... 128/204.23, 205.13
See application file for complete search history.

(56) References Cited

U.S. PATENT DOCUMENTS

2005/0284472 A1* 12/2005 Lin .................. A61M 16/0084 128/202.29
2008/0257351 A1* 10/2008 Gitschlag .......... A61M 16/0084 602/18

(Continued)

FOREIGN PATENT DOCUMENTS

DE 202020101614 U1 * 4/2020
WO WO-2021130737 A1 * 7/2021 ........ A61M 16/0084
WO WO-2021194345 A1 * 9/2021 ........ A61M 16/0057

OTHER PUBLICATIONS

Translation of DE-202020101614-U1. (Year: 2020).*

*Primary Examiner* — Paige Kathleen Bugg
(74) *Attorney, Agent, or Firm* — Klarquist Sparkman, LLP

(57) ABSTRACT

A breathe assist system is used with a breathe assist control system in providing air to a patient to assist with breathing. The breathe assist control system includes a pressure sensor configured to detect pressure within a patient mask indicative of patient inhalations and exhalations and a controller. The controller is connected to the pressure sensor and to an air supply device for supplying air to the patient mask. The controller receives a pressure signal indicating a pressure detected by the pressure sensor and sends a control signal to the air supply device to control supply of air to the patient mask. An associated breathe assist system and methods are also disclosed.

10 Claims, 11 Drawing Sheets

(56) References Cited

U.S. PATENT DOCUMENTS

| | | | | |
|---|---|---|---|---|
| 2011/0232641 | A1* | 9/2011 | Haggblom | A61M 16/12 128/204.21 |
| 2012/0145151 | A1* | 6/2012 | Bergman | A61M 16/0084 128/205.16 |
| 2019/0232016 | A1* | 8/2019 | Sayani | A61M 16/0003 |
| 2019/0336713 | A1* | 11/2019 | Piracha | A61M 16/0084 |
| 2020/0086075 | A1* | 3/2020 | Mujeeb-U-Rahaman | A61M 16/0003 |
| 2020/0353192 | A1* | 11/2020 | Fried | A61M 16/00 |
| 2021/0299378 | A1* | 9/2021 | Christenson | A61M 16/20 |
| 2021/0322692 | A1* | 10/2021 | Molander | A61M 16/201 |
| 2021/0330914 | A1* | 10/2021 | Young | A61M 16/161 |
| 2023/0166070 | A1* | 6/2023 | Wood | A61M 16/20 128/204.21 |
| 2023/0181850 | A1* | 6/2023 | Cooper | A61M 16/024 128/204.21 |

* cited by examiner

BREATHE ASSIST SYSTEM AND BREATHE ASSIST CONTROL SYSTEM

CROSS REFERENCE TO RELATED APPLICATION

This application claims the benefit of the earlier filing date of U.S. Provisional Patent Application No. 63/054,151, filed on Jul. 20, 2020, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

BACKGROUND

Described below are implementations of a breathe assist system and a breathe assist control system with one or more operating modes, such as for use with an emergency ventilator (e.g., a conventional Bag Valve Mask (BVM) device).

According to various implementations, the breathe assist system has a manual ventilation device having a mask for coupling to a patient, an inflation bag and a hose interconnecting the inflation bag and the mask to supply air from the bag to the patient, a mechanism to compress the inflation bag and a sensor configured to sense an exhalation pressure from the mask and to provide a control input to the mechanism to synchronize operation of the mechanism with the patient's breathing.

SUMMARY

According to some implementations, a breathe assist control system used with a breathe assist system to provide air to a patient includes a pressure sensor configured to detect a pressure within a patient mask indicative of patient inhalations and exhalations. The breathe assist control system also includes a controller connected to the pressure sensor and to an air supply device for supplying air to the patient mask. The controller receives the pressure signal indicating the pressure detected by the pressure sensor and sends a control signal to the air supply device to control supply of air to the patient mask.

The air supply device can comprise an inflation air bag and a movable member controllable to compress the inflation air bag. The air supply device can comprise a source of oxygen.

The breathe assist control system can also comprise a flow sensor configured to detect a flow rate of fluid through the patient mask.

The controller can be programmed to execute a patient breathe assist mode in which the air supply device is controlled to produce a breath synchronized with when the pressure signal indicates that the patient is attempting to inhale. The controller can be programmed to execute a manual mode in which the air supply device is configured to supply air to the patient according to at least one of a selected breaths per minute rate, an inhale/exhale rate and/or a total volume. The controller can be programmed to execute a modified patient breathe assist mode in which the air supply device is controlled to produce a breath synchronized with when the pressure signal indicates that the patient is attempting to inhale, modified by a predetermined minimum number of breaths to be produced by the air supply device even if sufficient patient inhalation attempts are not detected.

The controller can be configured to activate an alarm if the pressure is below a predetermined low pressure level. The predetermined low pressure level can be set to indicate that at least one of the patient mask or a hose is not properly connected. The controller can be programmed to detect a lung over-pressure condition if the pressure exceeds a predetermined maximum pressure. The controller can be configured to cause the air supply device to shut off if the lung over-pressure condition is detected.

The breathe assist control system can comprise a user interface and user controls, wherein the controller is configured to receive user input via the user controls and to display information on the user interface. The user interface can be configured to display at least one of a BPM (breaths per minute) value, an I/E (Inhalation over Exhalation rate) value, a VT (Total Volume of breath) value, a low pressure warning, a PKP (peak lung pressure) value and a current operating mode, as well as other information.

The breathe assist control system can comprise a visual and/or audio warning indicator, and the controller can be configured under predetermined conditions to cause the visual and/or audio warning indicator to operate to signal a warning to an operator.

The controller can be configured to receive a limit switch signal from a limit switch positioned to detect when a component of the air supply device reaches a limit condition.

The breathe assist control system can comprise a $CO_2$ sensor coupled to the mask that is configured to detect a $CO_2$ concentration in the patient's exhalations through the mask.

According to another implementation, a method of controlling a breathe assist system for assisting a patient comprises using a pressure sensor configured to detect pressure within a patient mask to detect pressures indicative of patient inhalations and exhalations, and controllably supplying air from an air supply device to the patient mask based on a pressure signal indicating pressures detected by the pressure sensor.

The air supply device can be controlled to produce a breath for the patient synchronized with when a pressure signal from the pressure sensor indicating that the patient is attempting to inhale.

The air supply device can be controlled to execute a manual mode in which the air supply device supplies air to the patient according to at least one of a selected breaths per minute rate, an inhale/exhale rate and/or a total volume. The air supply device can be controlled to execute a modified patient breathe assist mode in which the air supply device is controlled to produce a breath synchronized with when the pressure signal indicates that the patient is attempting to inhale, modified by a predetermined minimum number of breaths to be produced by the air supply device even if sufficient patient inhalation attempts are not detected.

The method can include triggering an indicator if the pressure is below a predetermined low pressure level. The predetermined low pressure level can be set to indicate that the patient mask and/or a hose is not properly connected.

The method can include determining if a lung over-pressure condition is reached if the pressure detected by the pressure sensor exceeds a predetermined maximum pressure, and automatically shutting off the air supply device if the lung over-pressure condition is detected.

According to another implementation, a breathe assist system to assist in providing air to a patient includes a patient mask through which air is configured to be supplied to the patient, an air supply device connected to the patient mask, the air supply device being controllable to supply air to the patient through the patient mask, a pressure sensor configured to detect a pressure within the patient mask indicative of patient inhalations and exhalations and a controller. The controller is connected to the pressure sensor and to the air supply device. The controller receives a pressure signal indicating the pressure detected by the pressure sensor and sends a control signal to the air supply device to selectively control the supply of air to the patient mask.

The air supply device can comprise a rotating motor and a link arm driven by the rotating motor in a reciprocating motion to compress an inflation air bag. The system can comprise a one-way valve and an air filter positioned between the inflation air bag and the mask. The system can comprise a flow sensor configured to detect a flow rate of fluid through the patient mask.

The controller can be programmed to execute a patient breathe assist mode in which the air supply device is controlled to produce a breath synchronized with when the pressure signal indicates that the patient is attempting to inhale. The controller can be programmed to execute a manual mode in which the air supply device is configured to supply air to the patient according to at least one of a selected breaths per minute rate, an inhale/exhale rate and/or a total volume. The controller can be programmed to execute a modified patient breathe assist mode in which the air supply device is controlled to produce a breath synchronized with when the pressure signal indicates that the patient is attempting to inhale, modified by a predetermined minimum number of breaths to be produced by the air supply device even if sufficient patient inhalation attempts are not detected.

The foregoing and other objects, features, and advantages of the invention will become more apparent from the following detailed description, which proceeds with reference to the accompanying figures.

DETAILED DESCRIPTION

Figure 1:
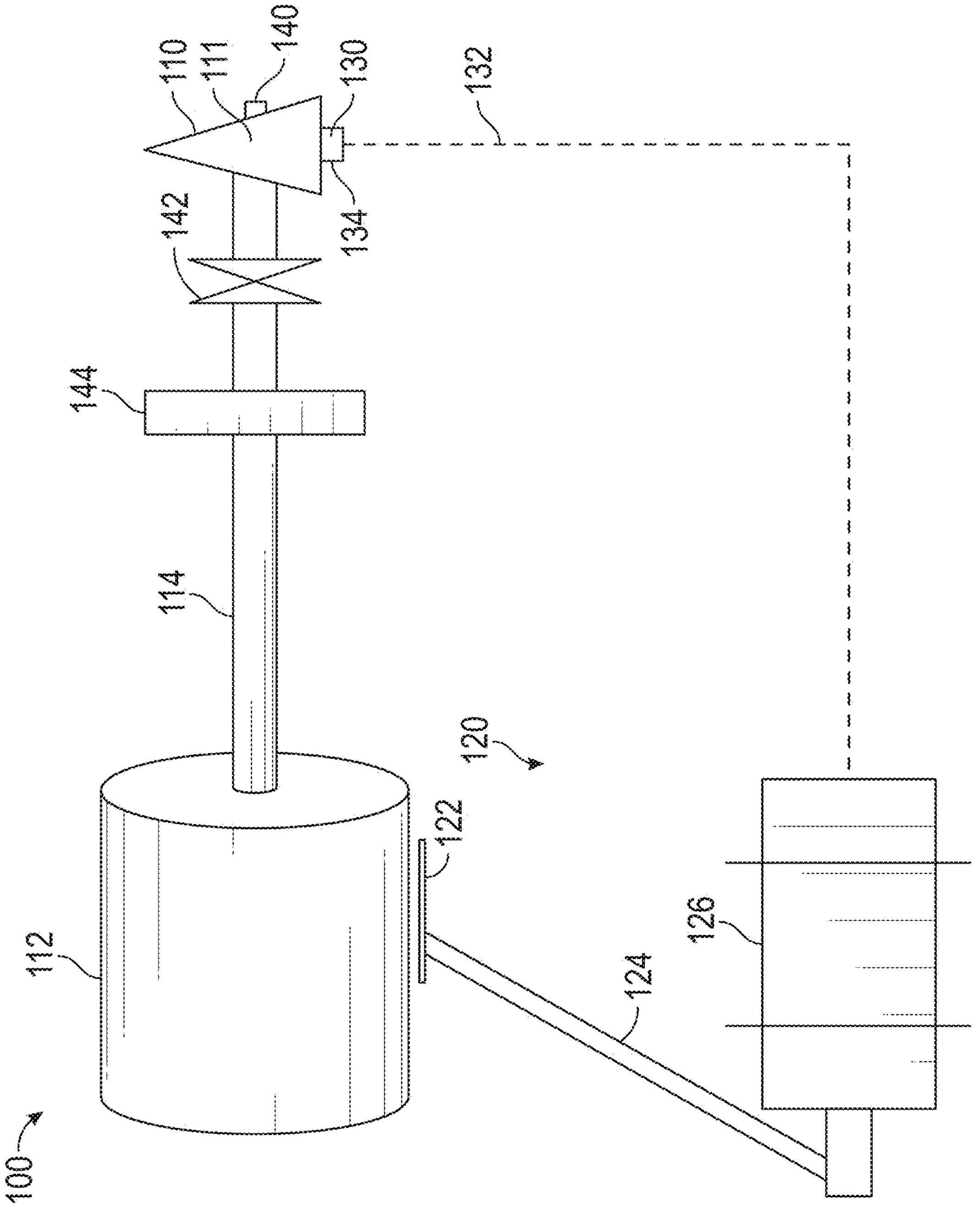
FIG. 1 is a schematic diagram showing an implementation of a breathe assist system.

Referring to FIG. 1, a breathe assist system 100 is shown schematically and includes a mask 110 for a patient, an inflation bag 112 and a hose 114 connecting the inflation bag 112 and the mask 110. The mask 110 typically includes a one-way valve 111. The mask 110, one-way valve 111 and inflation bag 112 may be a conventional BVM resuscitator device, also referred to as an Ambu® bag. In the conventional BVM device, an operator must manually compress the inflation bag 112 at a selected rate for the full duration of use.

In the breathe assist system 100, there is a mechanism 120 that is controllable to automatically compress the inflation bag 112. For example, the mechanism 120 may include a pusher member 122 shaped to contact the inflation bag 112, a link arm 124 connected to the pusher member 122 and a motor 126 that can be driven in rotation to cause the link arm to reciprocate, thereby causing the pusher member 122 to repeatedly compress the inflation bag 112. If a conventional BVM device is used, the safety features of that device are desirably maintained, even though it is mechanically actuated by the pusher member 122 rather than actuated by a practitioner's hand.

The mask 110 has an inhalation port to which the hose 114 is connected and an exhalation port 134 (also sometimes referred to as an expiration port). A pressure sensor 130 can be coupled to the mask to detect the patient's inhalations and exhalations. One or more outputs from the pressure sensor 130 can be connected to a controller and/or control system, such as is shown schematically by the control link 132 connecting the pressure sensor 130 to the motor 126 and/or mechanism 120. The pressure sensor 130 detects the patient's exhalations and inhalations. In addition, the pressure sensor 130 can be configured to provide an optional assisted control to synchronize operation of the mechanism 120 to provide breathing assistance in conjunction with the patient's own breathing.

As is described below in greater detail, a breathe assist control system can be used to control the system to produce selected output. For example, the mechanism 120 can be set to achieve a selected respiration rate (typically measured in breaths per minute). Further, the system 100 can be controlled to achieve a selected tidal flow. Tidal volume is defined as the lung volume representing the normal volume of air displaced between normal inhalation and exhalation when extra effort is not applied. Also, the system 100 can be controlled to achieve a desired I:E ratio (inspiratory time to expiratory time ratio).

As mentioned, the mask 110 typically has an exhalation port, such as the exhalation port 134, through which the patient's exhalations are exhausted. The mask 110 can be fitted with an optional $CO_2$ sensor 140 to detect a concentration of $CO_2$ in the patient's exhalations.

The system 100 can include an optional flow sensor 142 for sensing a flow rate of air supplied through the hose 114. The flow sensor 142 can be hot wire anemometer type positioned to sense flow into and out of the patient mask. Also, the system 100 can include an optional filter 144 that filters the air supplied through the hose 114. Optionally, a PEEP (Positive End-Expiratory Pressure) sensor (FIG. 2) can be fitted.

Figure 2:
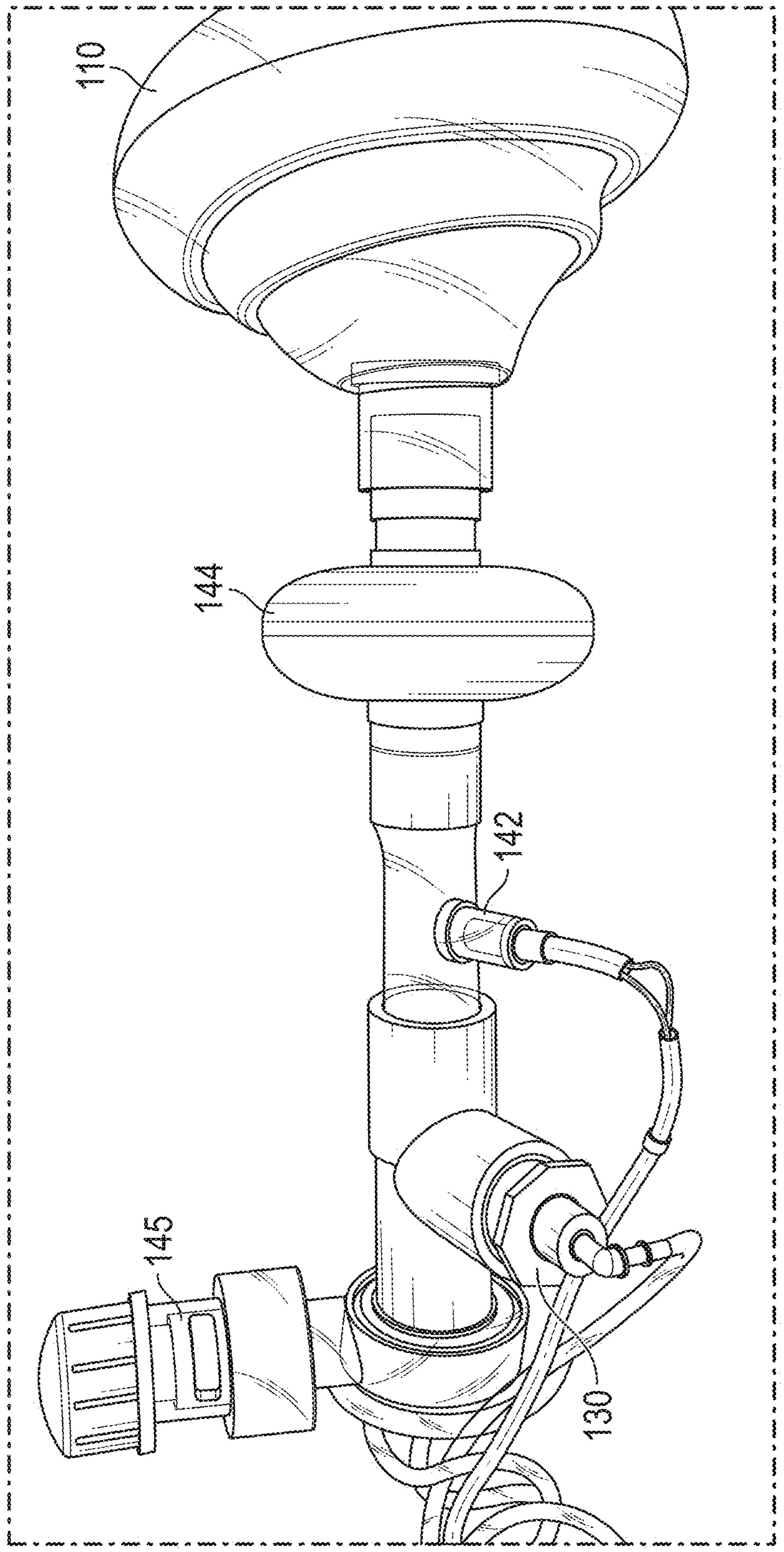
FIG. 2 is a perspective view of a representative patient mask and other components.

A representative arrangement of the mask 110 and other components is shown in FIG. 2. FIG. 2 shows the air filter 144 connected upstream of the inhalation port of the mask 110. The optional flow sensor 142 and the pressure sensor 130 can also be positioned upstream of the mask 110 along an interconnecting hose. As also shown in FIG. 2, the arrangement has a PEEP valve 145.

Figure 3:
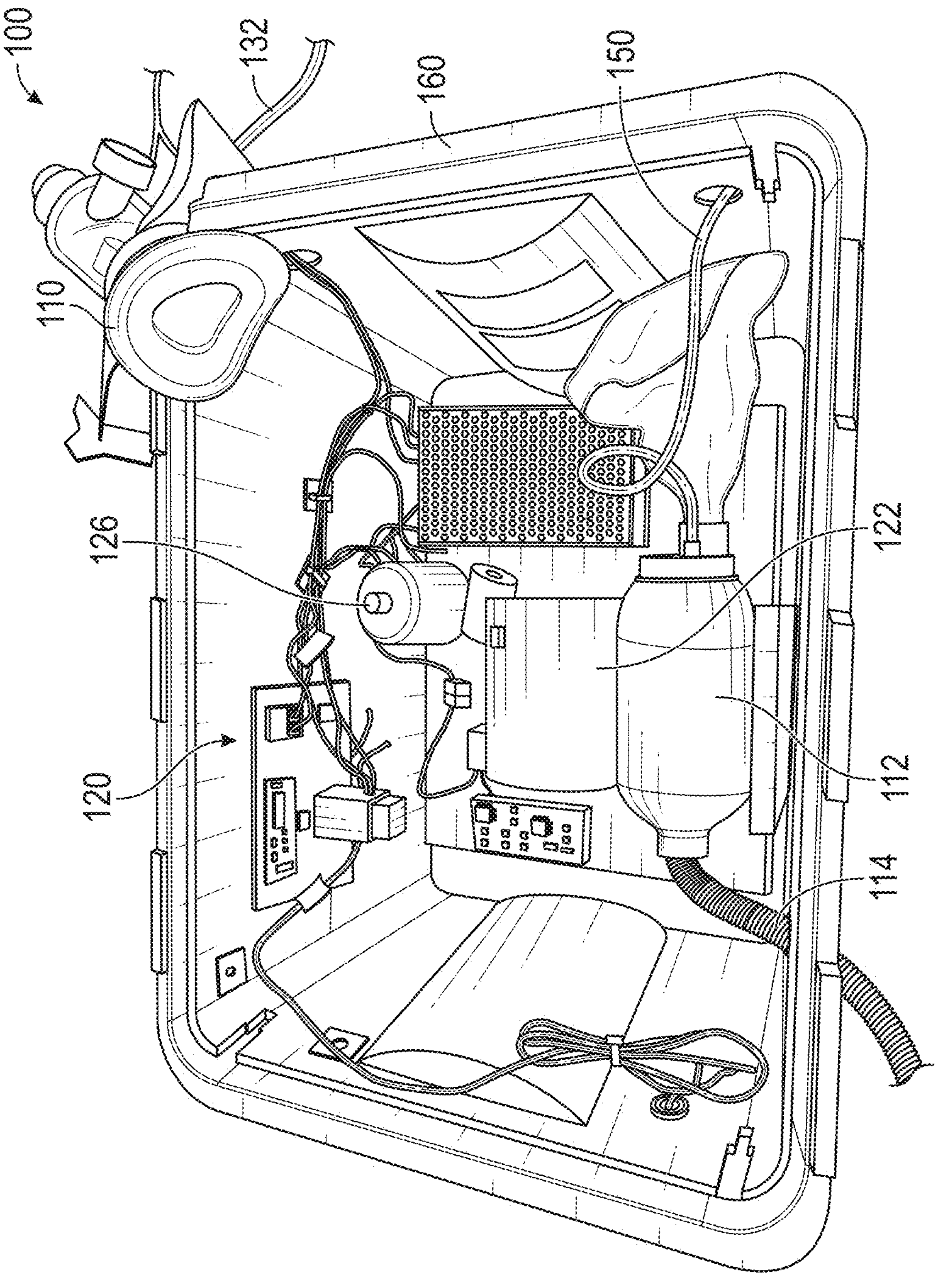
FIG. 3 is a plan view of an implementation of a breathe assist system.
Figure 4:
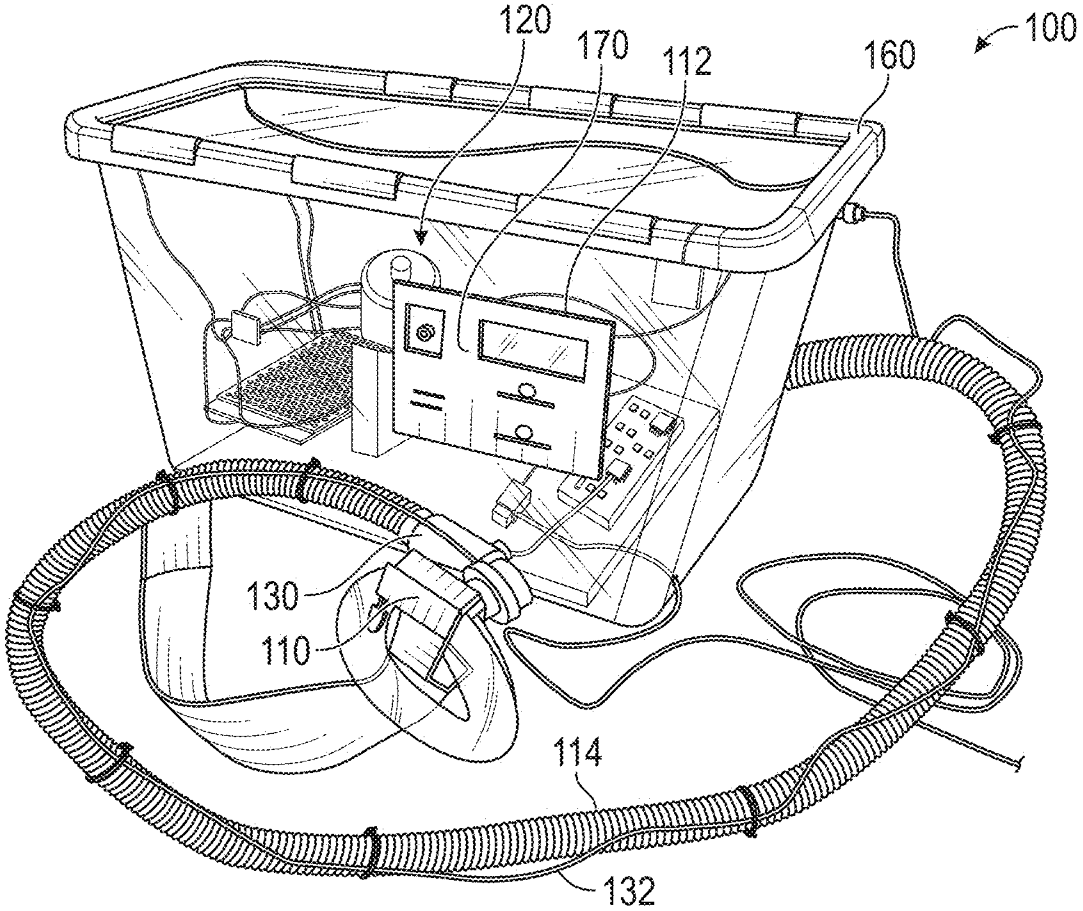
FIG. 4 is a perspective view of the breathe assist system of FIG. 3.

FIGS. 3 and 4 show an additional embodiment of the system 100. In addition to the mask 110, inflation bag 112, hose 114 and mechanism 120, FIGS. 3 and 4 show that components can be provided in an enclosure 160. In addition, the control link 132 can be provided as a hard-wired connection that is optionally routed along the hose 114 (FIG. 4). Further, the inflation bag 112 can have a connection 150 to a source of oxygen to supplement or replace the air that is normally drawn into the inflation bag.

Referring to FIG. 3, the pusher member 122 can be fabricated with a semi-cylindrical outer surface, such as from a section of PVC pipe. The motor 126 can be an automotive windshield wiper motor or other similar conventional motor. Referring to FIG. 4, the control circuit for the system 100 can include a control panel 170 having a display and one or more control elements for adjustably controlling the system 100.

Figure 5:
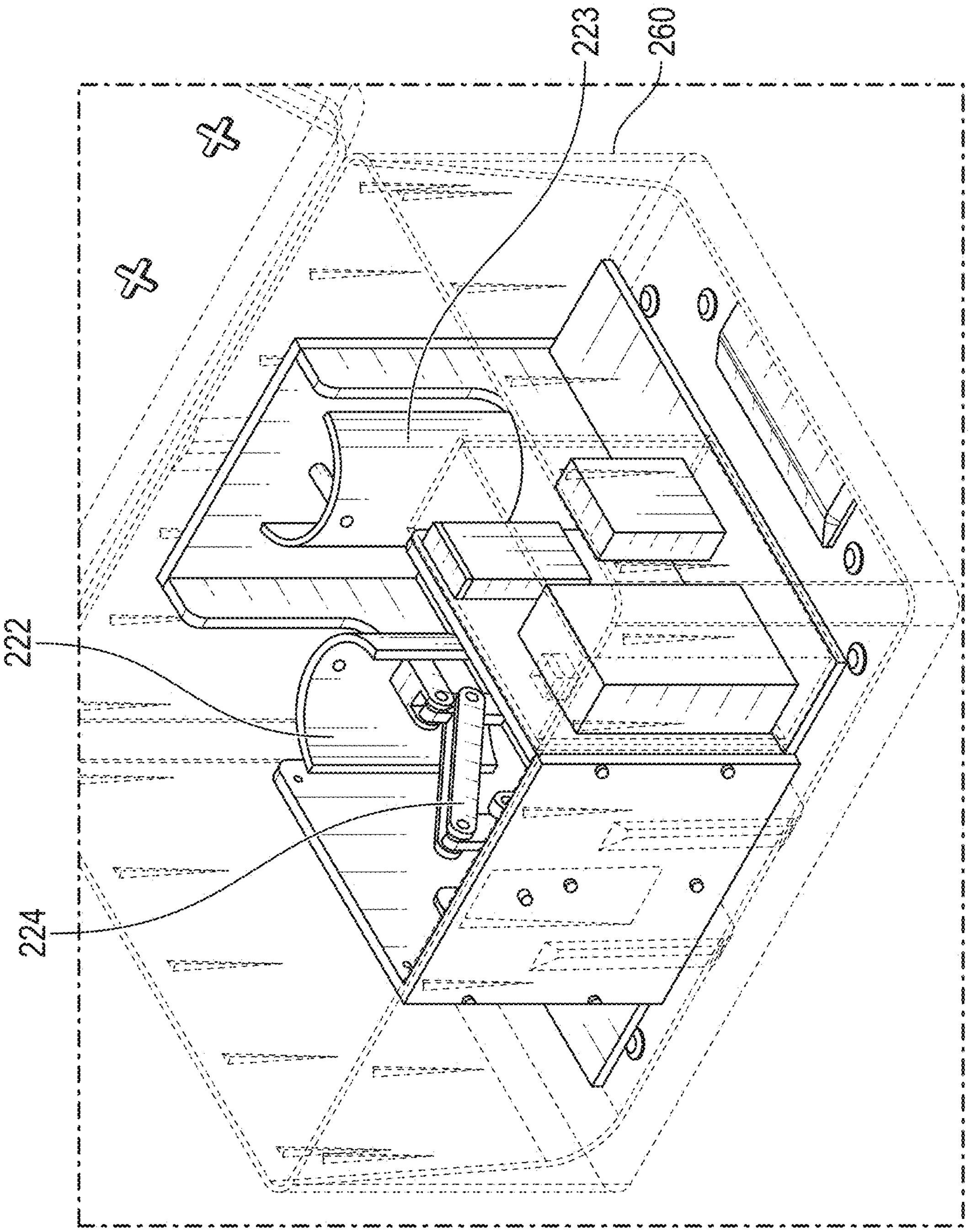
FIGS. 5-12 are partial perspective views of another implementation of a breathe assist system.
Figure 6:
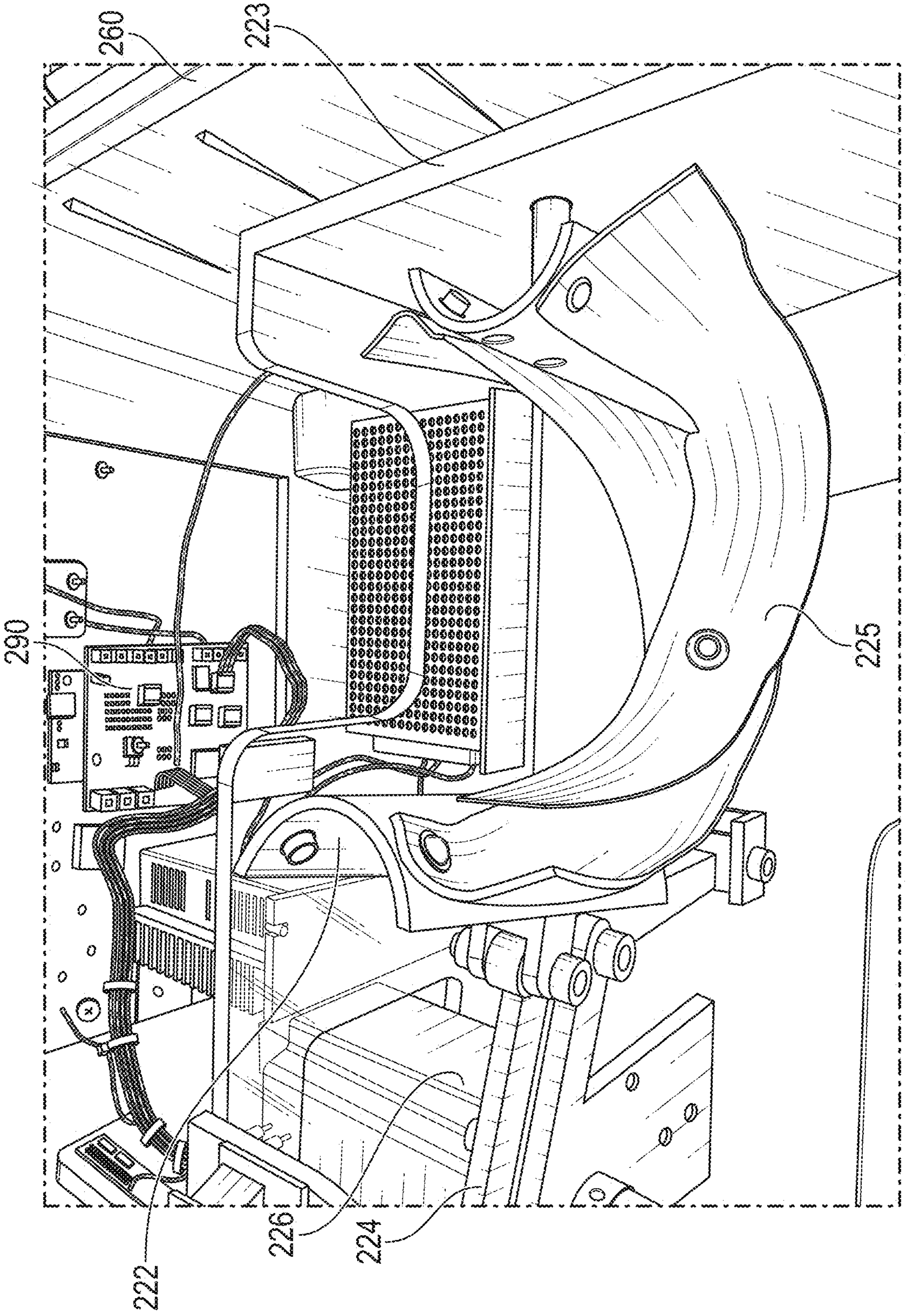
Figure 7:
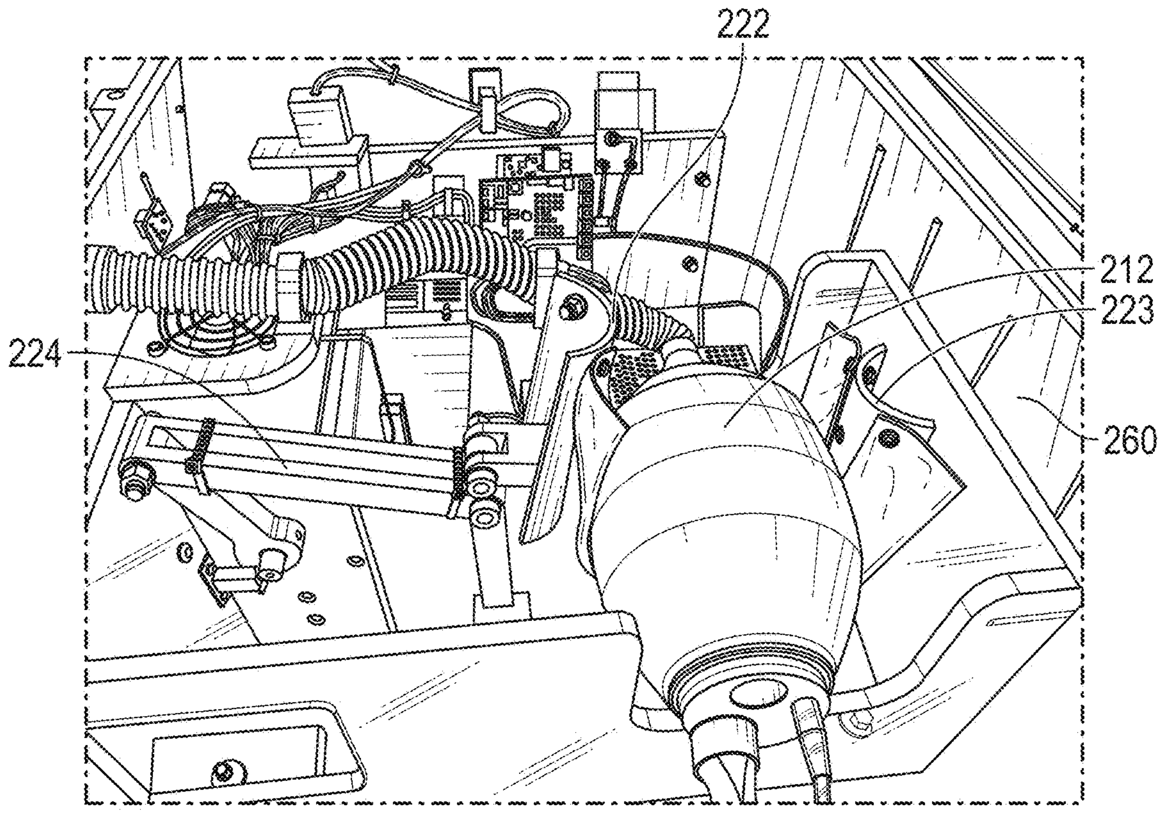
Figure 8:
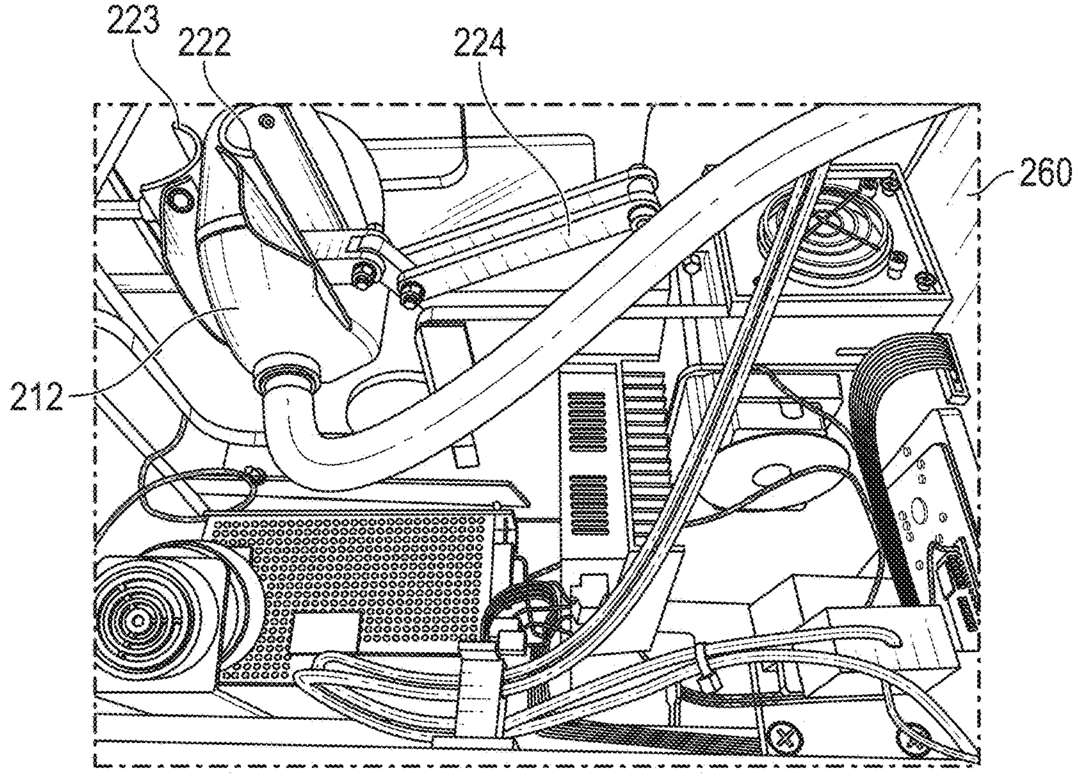
Figure 9:
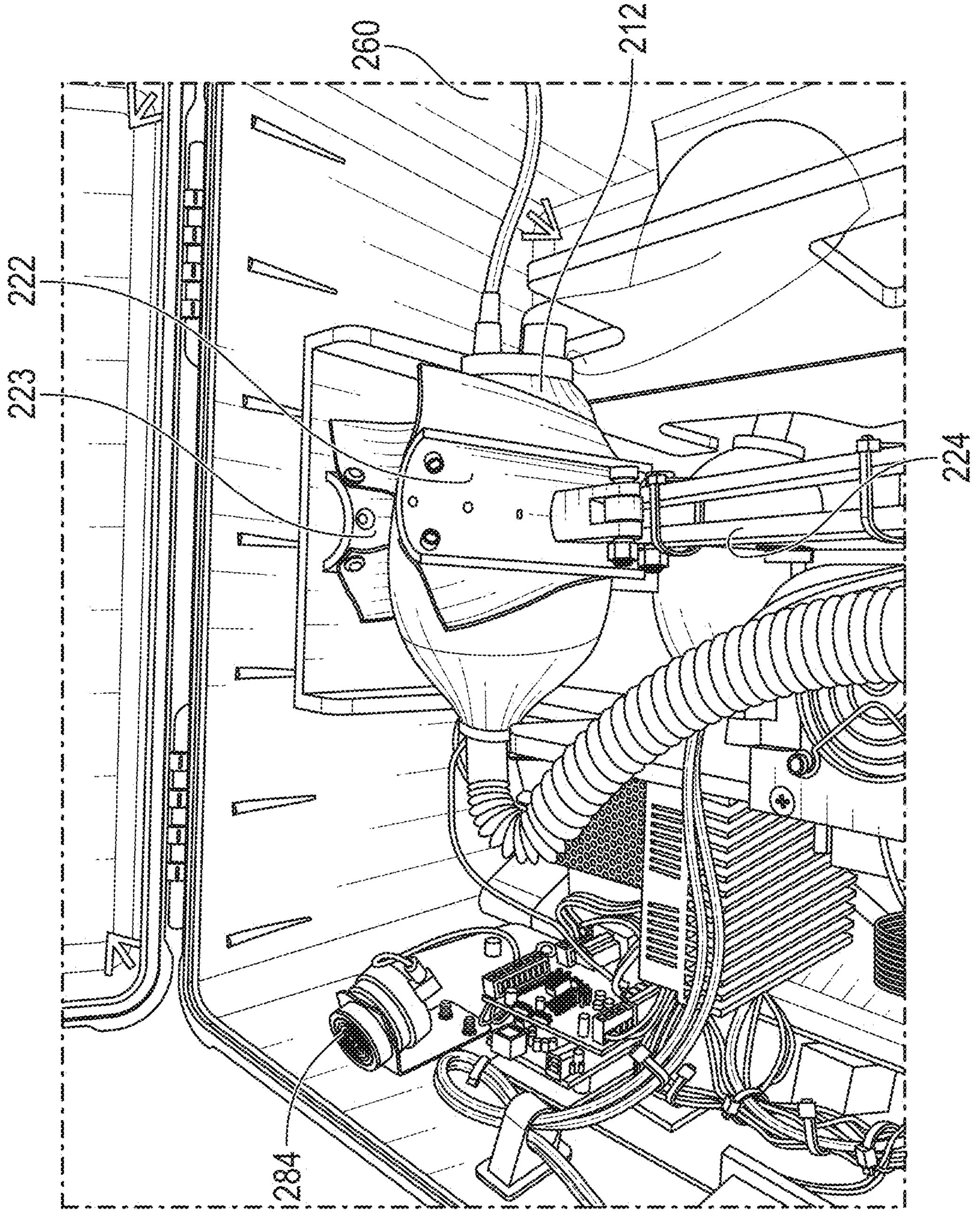

FIG. 5 is a perspective view showing another implementation with a dedicated enclosure 260, a stationary inflation bag side member 223 opposite a movable pusher member 222, a different link arm assembly 224 and a stepper motor 226, among other features. Although not specifically shown, the implementation of FIGS. 5-12 is also for use with the mask 110 and other components as shown in FIG. 2 and described above, and can also have a connection to a source of oxygen to supplement or replace the air that is normally drawn into the inflation bag. FIG. 6 is a perspective view from another angle showing a cradle 225 between the movable pusher member 222 and the stationary inflation bag side member 223 that is sized to receive an inflation bag. As also shown in FIG. 6, the enclosure 260 houses circuit board(s) and other electronic and electrical components 290 for the system, including the components 290*a*-290*e* described in greater detail below. FIGS. 7 and 9 show an inflation bag 212 in its position within the cradle 225 from two different angles, and while the inflation bag 212 is not being compressed. FIG. 8 shows the inflation bag 212 being compressed by the movable pusher member 222.

Figure 10:
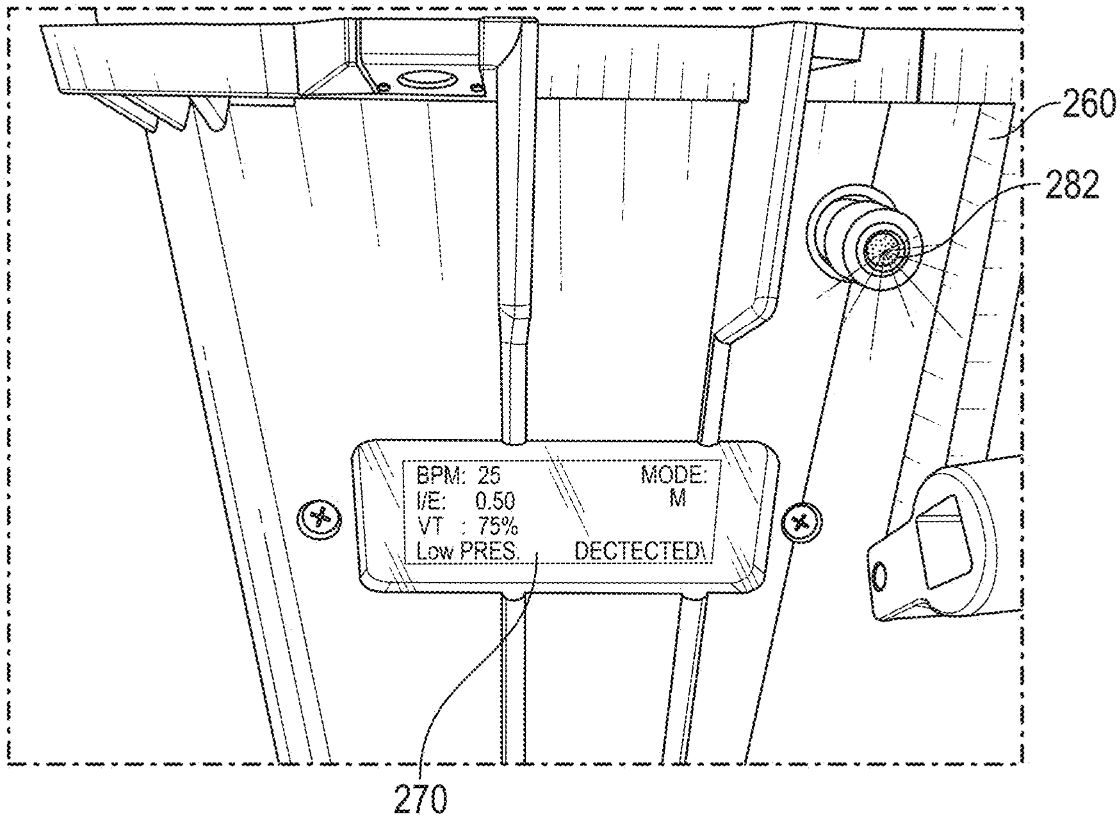
Figure 11:
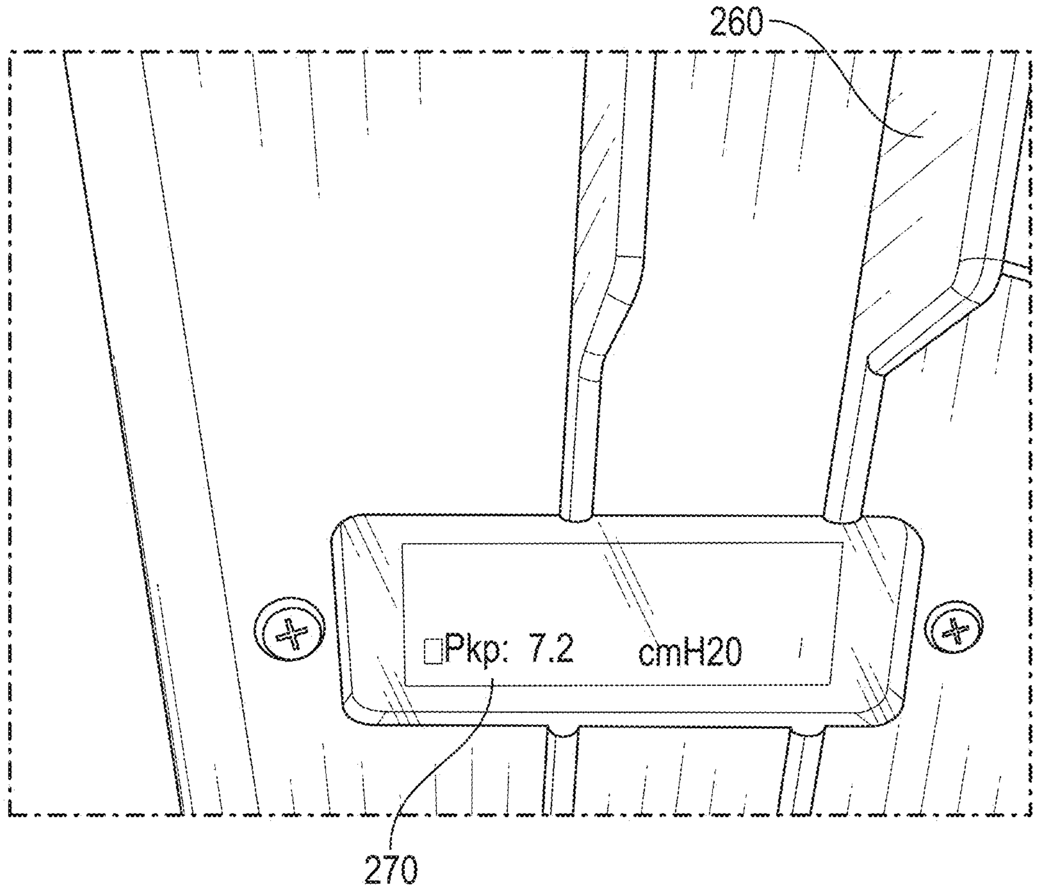
Figure 12:
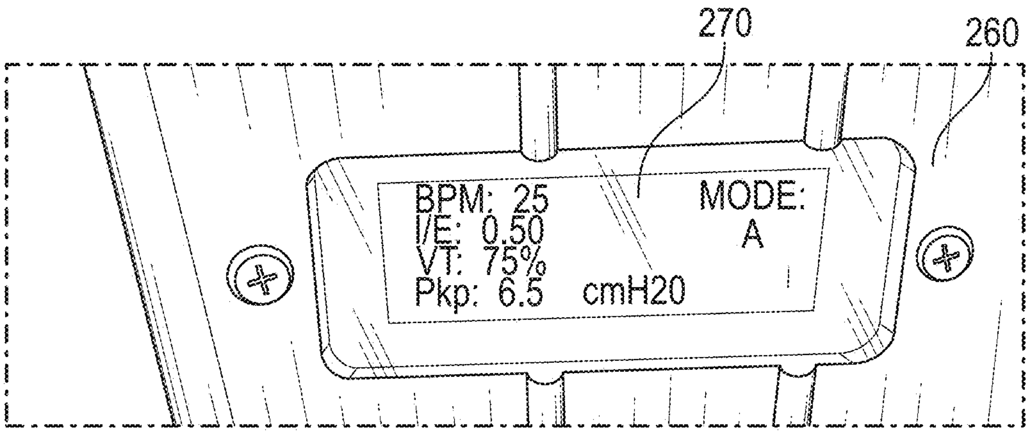

FIGS. 10, 11 and 12 show a user interface 270 (e.g., a display screen and controls) displaying various parameters and other information to an operator. For example, the user interface 270 can display one or more of: a BPM (breaths per minute) value, an I/E (Inhalation over Exhalation rate) value, a VT (Total Volume of breath) value, and a current operating mode (e.g., "M" for manual mode, as is discussed below in more detail).

In FIG. 10, a low pressure detected warning is displayed, based on the detected pressure being lower than a predetermined minimum pressure, which can correspond to a condition where the mask and/or hose has become disconnected. The low pressure condition can be further signaled to the operator by a visual indicator 282, e.g., by illumination, and/or an audio indicator (alarm) 284 (FIG. 9).

FIG. 11 shows the user interface displaying a PKP (peak lung pressure) value. FIG. 12 shows the user interface 270 indicating parameters during a different state of operation from that of FIG. 10 or FIG. 11, and also showing that an Assist mode ("A") has been selected. Any suitable physical user controls (not shown) or a touch screen can be used to input selections for operating the system.

Figure 13:
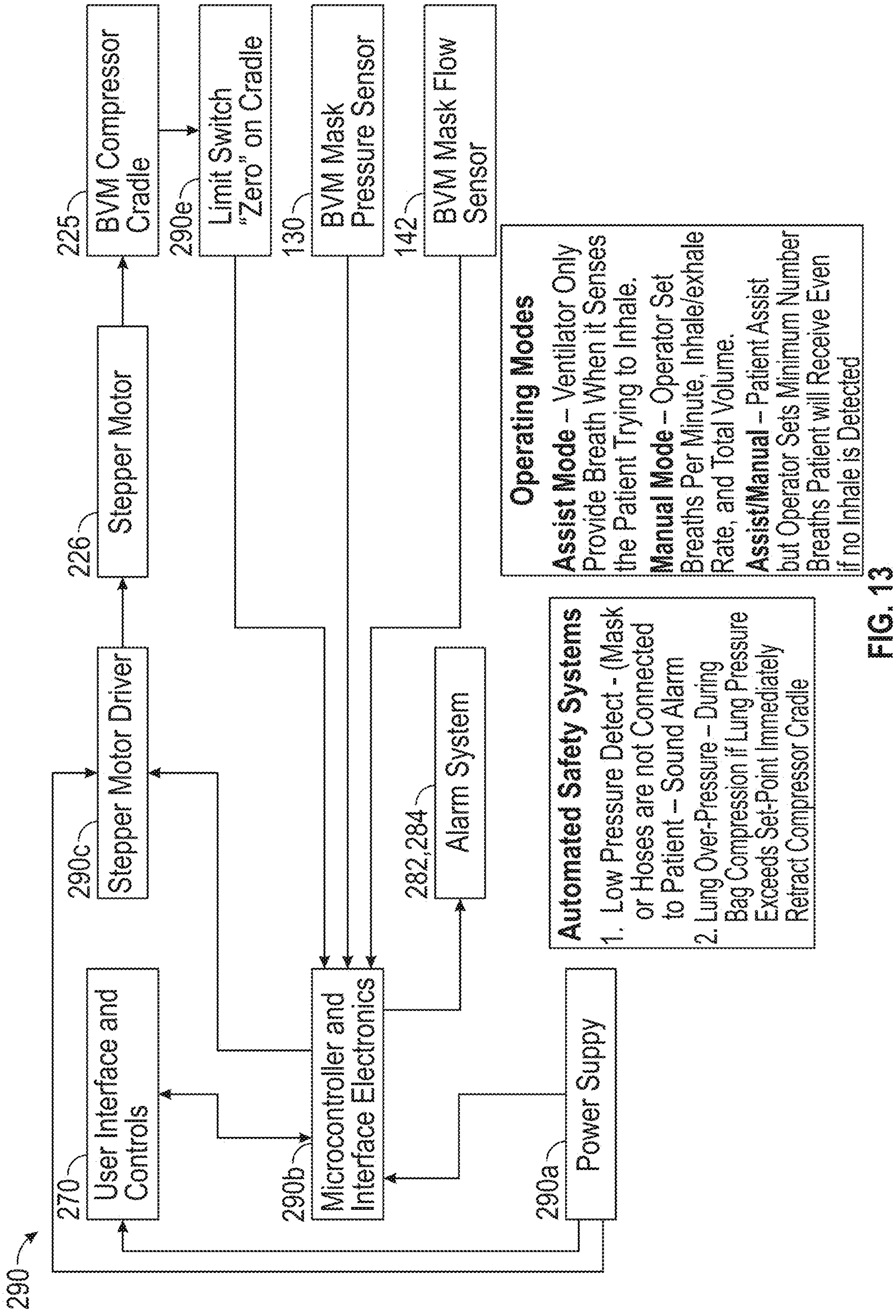
FIG. 13 is a block diagram of an implementation of the breathe assist control system.

FIG. 13 is a block diagram of the breathe assist system illustrating an implementation of the breathe assist control system and representative operating modes. A controller 290*b*, such as a microcontroller, receives a pressure signal input from the pressure sensor 130 of the mask 110. If provided, the controller 290*b* also receives a flow signal input from the flow sensor 142. As shown in FIG. 13, the controller 290*b*, the user interface 270 and the stepper motor 226 (through a stepper motor driver 290*c*), receive power from a power supply 290*a*. A limit switch 290*e* coupled to the cradle 225 is connected to provide its output to the controller 290*b*.

The controller 290*b* is programmed (or configured) to carry out various system operations, including at least three operating modes. In an Assist (or Patient Breathe Assist) mode, the system is controlled to only provide a breath (i.e., to compress the inflation bag 212) when the controller 290*b* determines, based on the pressure signal input, that the patient is attempting to inhale. In a Manual mode, the operator sets a breath rate (a BPM value), an inhale/exhale rate (an I/E value) and a total volume of breath (a VT value), and the system is operated to achieve these parameters. In a Modified Patient Breathe Assist mode (also sometimes referred to as an Assist/Manual mode), the system is controlled to only provide a breath when the patient is attempting to inhale, but a minimum number of breaths is provided even if no inhalation by the patient is detected, according to a setting selected by an operator.

From the standpoint of patient safety, the control system can also be configured to detect certain conditions and execute specified operations automatically. As described above, a low pressure condition can be determined by comparing the detected pressure to a predetermined minimum pressure. If the detected pressure is below the minimum pressure, a visual indicator and/or audio alarm can be triggered to signal the operator that the patient mask and/or the hose may be disconnected. As a second example, the controller can be programmed to detect if the pressure exceeds a predetermined maximum pressure. If the predetermined maximum pressure is exceeded, then the movable pusher member 222 and/or cradle 225 can be immediately released from compressing the inflation bag 212.

In some implementations, the new system and methods were implemented in an Arduino Mega 2560 microcontroller board with a custom shield PCB (printed circuit board) to control a ventilator. The code, which is an operating system, was written in C++.

The firmware implements an event-driven, pseudo-real-time state machine for controlling the ventilator stepper motor and ingesting data from the pressure sensor and the flow sensor, as well as the user interface controls on the front panel of the device.

The following methods are defined:

setup( )
- Configures system at power-up or reset for operation.
- Gets pressure baseline from sensor data.
- Initializes event queue.
- Kicks off breathing event chain.

loop( )
- This is the idle loop that runs whenever no events or ISRs are being serviced.
- Checks for event ripeness and user inputs.

eventHandler( )
- This is the umbrella function that processes events that have been extracted from the event queue.
- There are event handlers for "Motor Pulse Start Events," "Motor Pulse Stop Events," "Pressure Start Conversion Events," "Pressure Read Data Events," "Heart Beat Data Events," "Trigger Breath Events," "UI Timeout Events," "Motor Full Open Events," "Motor Full Open Timeout Events," "Motor Find Limit Events," "Motor Find Limit Timeout Events," "No Event Events," and "Unrecognized Events."

serialInputHandler( )
- This method takes characters received from keyboard input (used for diagnostics only) and translates them into changes in variables and parameters in the code.

checkUIFlags( )
- This method is called during the main loop and looks to see if any UI widget ISRs have triggered and need servicing, i.e., if the rotary encoder has been rotated or a button has been pressed.

openLimitSwitch_ISR( )
- ISR gets called when then the motor limit switch 290*e* (FIG. 13) changes state.

encoderButton_ISR( )

This ISR gets called whenever the front panel button is pressed.

encoderRotation_ISR( )

This ISR gets called whenever the front panel encoder is turned (rotated).

readConfigFromEEPROM( )

This method reads the contents of the EEPROM and sets the state variables based on the last known good configuration.

writeConfigToEEPROM( )

This method writes the current state variables to the EEPROM so that the system will come back in the same state it left in the case of a power glitch.

setEncoderLED( )

This method sets the color of the RGB LED built into the encoder wheel.

lcdUpdate( )

This method updates the contents of the of the front panel LCD screen. update BreathParameters( )

This method calculates breath timing, motor pulse counts, and motor pulse lengths based on parameters that can be modified via the user interface.

getMotorHome( )

This method returns whether or not the motor is in its home position. calibrateBaselinePressure( )

This method takes a series if pressure measurements and returns the standard deviation of the samples. This is part of the baseline detection code called during setup ( )

timestamp( )

This method returns the number of microseconds since power-on.

addEvent( )

This method adds an event to the priority event queue.

getEvent( )

This method removes the first event from the priority event queue and returns its type removeEvent( )

This method removes the first event of a particular type from the priority event queue.

update Event( )

This method updates the timestamp associated with the first event of a particular type from the priority event queue.

wdreset( )

This method resets the watchdog timer to prevent self-reset.

detectColdStart( )

This method checks for RAM artifacts that indicate that this was a warm restart. If not found, it creates the RAM artifacts.

PrintResetSource( )

This method prints the reset source to the serial port.

W00t( )

This method sends the encoder wheel through a rainbow display of pure RGB power.

In some implementations, the pressure sensor 130 is a Honeywell MPRLS sensor. Such a sensor is a very small piezoresistive sensor offering a digital output for reading pressure over the full specified range. In some implementations, the driver for the sensor can be modified to allow synchronous non-blocking transactions.

As described above, a low cost, easy to fabricate ventilator or breathing assistance system is provided, which could keep many COVID-19 patients out of the ICU and, if possible, out of the hospital altogether, among other beneficial uses. The system has the dual benefit of providing direct breathing assistance to patients and limiting the exposure of hospital staff to contagious individuals.

The system may be employed in the event of a crisis situation where hospitals are overwhelmed and/or traditional ventilation options are not available. If the system is available in large enough numbers, it could also enable different protocols for patient management. More patients could be given breathing assistance earlier, potentially keeping them away from the hospital longer. Importantly, the system increases the options for treating patients out of the ICU or traditional hospital environments.

As described, the system builds off the conventional BVM (Bag Valve Mask) manual resuscitator readily available in ambulance and medical settings. Instead of a human operator, an electronically controlled compression system is used. This provides greater operational control over longer periods of time while taking advantage of safety features already designed into the conventional BVM. These safety features include:

Pressure release valve (<60 cm $H_2O$)

PEEP range is limited.

Use of I:E ratio is important to avoid "breath stacking."

Viral/HEPA filters integrated in BVM

In a hospital setting, the system would be readily connectible to oxygen lines and/or other monitoring/medical systems, and operated under expert medical staff attention. The use of viral and/or HEPA filters is already integrated in commercial BVM designs and is important to limit staff exposure. Sedation and intubation using a standard ventilator is possible if necessary.

Outside of a hospital setting, or in a field hospital, sedation and intubation may not be possible. A portable oxygen source is necessary, either through an oxygen concentrator or cylinder, which are readily available. Efforts should be made to achieve the best mask seal possible, and viral filters would still be utilized. Additional steps could be taken to reduce possible exposure including use of containment devices, e.g., a CPAP "helmet" or similar device. In a field hospital setting, where patients are already sick and other environmental controls may be implemented, e.g., negative pressure tents with filters, this may not be necessary.

In some implementations the system can be "tuned" to the patient's breathing. These include the depth of breath (adjusting % bag compression), respiratory rate and inspiration/expiration ratio to achieve a stable cycle. Example control features include the following:

Tidal Volume (% compression of bag-calibrated for volume (200-800 mL))

Respiratory Rate (8-30 BPM-breaths per minute)

Inspiration: Expiration ratio (range of 1:1 to 1:4)

Manually adjusted PEEP valve pressure (integrated in BVM 5-15 cm $H_2O$)

In some implementations, as described above, the pressure sensor 130 or a similar approach is used to implement patient-triggered cycle initiation for better synchronization. Unlike other BVM systems, the present invention provides a breathing assist mode so that the mechanically actuated operation can be synchronized with the patient's breathing using a low-cost sensor and/or transducer and new control logic/control software. In other BVM systems, breathing assistance that is not synchronized with the patient's breathing can interfere with independent breathing and cause discomfort and, in extreme cases, injury.

Fully conscious patients can use the present system instead of being intubated, yet still receive breathing assistance with control of PIP, PEEP, tidal volume and respiratory rate. The system senses the patient's attempt to take a breath and the synchronizes that attempt with the mechanically assisted compression of the inflation bag. Effectiveness, comfort and level of safety for the patient are enhanced. In some cases, intubation-based therapy can be avoided, which is also beneficial to the patient.

In view of the many possible embodiments to which the principles of the disclosed invention may be applied, it should be recognized that the illustrated embodiments are only preferred examples and should not be taken as limiting the scope of protection. Rather, the scope is defined by the following claims. We therefore claim all that comes within the scope and spirit of these claims.

We claim:

1. A breathe assist control system to assist in providing air to a patient, comprising:

a pressure sensor configured to detect a pressure within a patient mask indicative of patient inhalations and exhalations;

a flow sensor configured to detect a flow rate of fluid through the patient mask;

a $CO_2$ sensor coupled to the patient mask that is configured to detect a $CO_2$ concentration in the patient's exhalations through the patient mask;

an air supply device comprising an inflation air bag, a movable member, a stationary member and a flexible cradle for supporting the inflation air bag between the movable member and the stationary member, wherein the movable member is controllable to compress the inflation air bag against the stationary member, and wherein the flexible cradle comprises a pair of crossed straps that directly engage the inflation air bag;

a controller connected to the pressure sensor and to the air supply device for supplying air to the patient mask, the controller receiving a pressure signal indicating the pressure detected by the pressure sensor and sending a control signal to the air supply device to control the supplying of air to the patient mask, wherein the controller is programmed to execute:

a manual mode in which the air supply device is configured to supply air to the patient according to at least one of a selected breaths per minute rate, an inhale/exhale rate and/or a total volume, a patient breathe assist mode in which the air supply device is controlled to produce a breath synchronized with when the pressure signal indicates that the patient is attempting to inhale, and a modified patient breathe assist mode in which the air supply device is controlled to produce a breath synchronized with when the pressure signal indicates that the patient is attempting to inhale, modified by a predetermined minimum number of breaths to be produced by the air supply device even if sufficient patient inhalation attempts are not detected.

2. The breathe assist control system of claim 1, wherein the controller is programmed to activate an alarm if the pressure is below a predetermined low pressure level set to indicate that at least one of the patient mask or a hose is not properly connected.

3. The breathe assist control system of claim 1, wherein the controller is programmed to detect a lung over-pressure condition if the pressure exceeds a predetermined maximum pressure and the controller is, optionally, programmed to cause the air supply device to shut off if the lung over-pressure condition is detected.

4. The breathe assist control system of claim 1, further comprising a user interface and user controls, wherein the controller is programmed to receive user input via the user controls and to display information on the user interface.

5. The breathe assist control system of claim 4, wherein the user interface is configured to display at least one of a BPM (breaths per minute) value, an I/E (Inhalation over Exhalation rate) value, a VT (Total Volume of breath) value, a low pressure warning, a PKP (peak lung pressure) value and a current operating mode.

6. The breathe assist control system of claim 1, further comprising a visual and/or audio warning indicator, and wherein the controller is programmed to cause the visual and/or audio warning indicator to operate under predetermined conditions to signal a warning to an operator.

7. The breathe assist control system of claim 1, wherein the controller is programmed to receive a limit switch signal from a limit switch positioned to detect when a component of the air supply device reaches a limit condition.

8. A breathe assist system to assist in providing air to a patient, comprising:

a patient mask through which air is configured to be supplied to the patient;

a pressure sensor configured to detect a pressure within the patient mask indicative of patient inhalations and exhalations;

a flow sensor configured to detect a flow rate of fluid through the patient mask;

a $CO_2$ sensor coupled to the patient mask that is configured to detect a $CO_2$ concentration in the patient's exhalations through the patient mask;

an air supply device connected to the patient mask, the air supply device comprising an inflation air bag, a movable member, a stationary member and a flexible air bag support member extending between the movable member and the stationary member and under a central region of the inflation air bag to hold the inflation air bag between the movable member and the stationary member, wherein the movable member is controllable to compress the inflation air bag against the stationary member to supply air to the patient through the patient mask; and a controller connected to the pressure sensor and to the air supply device, the controller receiving a pressure signal indicating the pressure detected by the pressure sensor and sending a control signal to the air supply device to selectively control the supply of air to the patient mask, wherein the controller is programmed to execute:

a manual mode in which the air supply device is configured to supply air to the patient according to at least one of a selected breaths per minute rate, an inhale/exhale rate and/or a total volume, a patient breathe assist mode in which the air supply device is controlled to produce a breath synchronized with when the pressure signal indicates that the patient is attempting to inhale, and a modified patient breathe assist mode in which the air supply device is controlled to produce a breath synchronized with when the pressure signal indicates that the patient is attempting to inhale, modified by a predetermined minimum number of breaths to be produced by the air supply device even if sufficient patient inhalation attempts are not detected.

9. The breathe assist system of claim 8, wherein the air supply device comprises a rotating motor and a link arm driven by the rotating motor in a reciprocating motion to move the movable member.

10. The breathe assist system of claim 9, further comprising a one-way valve and an air filter positioned between the inflation air bag and the patient mask.

* * * * *